(12) United States Patent
Fein et al.

(10) Patent No.: US 8,958,447 B2
(45) Date of Patent: *Feb. 17, 2015

(54) SYSTEM AND METHOD FOR LASERS IN SURGICAL APPLICATIONS

(71) Applicant: Lumenis Ltd., Yokneam Ilit (IL)

(72) Inventors: Asa Fein, Moshav Shchenia (IL); Alon Goldring, Tel Aviv (IL)

(73) Assignee: Lumenis Ltd. (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/025,667

(22) Filed: Sep. 12, 2013

(65) Prior Publication Data

US 2014/0018781 A1 Jan. 16, 2014

Related U.S. Application Data

(63) Continuation of application No. 12/363,410, filed on Jan. 30, 2009, now Pat. No. 8,559,473.

(60) Provisional application No. 61/063,340, filed on Feb. 1, 2008.

(51) Int. Cl.
  *H01S 3/00* (2006.01)
  *A61B 18/22* (2006.01)

(52) U.S. Cl.
  CPC .. *A61B 18/22* (2013.01); *H01S 3/00* (2013.01)
  USPC .................................. 372/33; 372/69; 372/81

(58) Field of Classification Search
  CPC ........................................................ H01S 3/00
  USPC ................................................ 372/33, 69, 81
  See application file for complete search history.

(56) References Cited

U.S. PATENT DOCUMENTS 6,083,217 A  7/2000  Tankovich

OTHER PUBLICATIONS

Irvine et al., "Infrared Optical Properties of Water and Ice Spheres", *Icarus*, 8:324-360 (1968).
McCaughey et al., "Compact Infrared Laser for Stapedotomy", *SPIE*, 68:42:1-6 (2008).
Patel et al., "CW Laser Action on the rotational Transition of the Sigma+ u-Sigma + g Vibrational Band of $CO_2$", *Bulletin of the American Physical Society*, 9, p. 500; Abstract #KC5 (1964).
Patel, C.K.N. , "Continuous-Wave Laser Action on Vibrational-Rotational Transitions of $CO_2$", *Physical Rev.*, 136(5A):A1187-A1193(1964).
Patel, C.K.N. ,"Interpretation of $CO_2$ Optical Maser Experiments", *Physical Rev, Letters*, 12(21):598-590 (1964).

*Primary Examiner* — Shawquia Jackson
(74) *Attorney, Agent, or Firm* — ISUS Intellectual Property PLLC

(57) ABSTRACT

Disclosed is a surgical laser system. The system includes a laser generator to generate laser radiation to cause water absorption levels that approximate water absorption levels achieved with a $CO_2$ laser, and one or more fibers coupled to the laser generator to deliver the generated laser radiation. In some embodiments, the laser generator is configured to generate radiation at multiple possible wavelengths in a range of between about 2.4 μm to about 2.75 μm.

15 Claims, 3 Drawing Sheets

SYSTEM AND METHOD FOR LASERS IN SURGICAL APPLICATIONS

CROSS-REFERENCE TO RELATED APPLICATIONS

This application is a continuation application which claims priority to U.S. application Ser. No. 12/363,410 filed on Jan. 30, 2009, which claims priority to provisional U.S. application Ser. No. 61/063,340, entitled "Device and Method for Lasers in Surgical Applications," filed Feb. 1, 2008, the content of which is hereby incorporated by reference in its entirety.

BACKGROUND OF THE INVENTION

The present disclosure generally relates to a laser for surgical applications. More particularly, the present disclosure relates to non-$CO_2$ laser generators (e.g., non-C02 laser devices, implemented, for example, based on quantum-well diode arrays) that achieve approximately the same water absorption levels typically produced by a C02 laser. By achieving the approximate absorption levels of water of those produced by C02 lasers without using a C02 laser, surgical operations can be accomplished with heretofore unrealized results.

The $CO_2$ laser was described by Patel et al. (see, for example, C. K. N. Patel, W. L. Faust and R. A Mcfarlane, "CW Laser Action on Rotational Transitions of the +u +g Vibrational Band of $CO_2$", Bulletin of American Physical Society 9, 500 (1964), and C. K. N. Patel, "Interpretation of C02 Optical Maser Experiments," Physical Review Letters 12, 21, 588-590 (1964))

Preliminary laboratory studies using a 20 W $CO_2$ laser for liver surgery in dogs were reported in 1966. The $CO_2$ laser is used in a wide variety of surgical operations in various fields including otolaryngology, gynecology, aesthetic dermatology, neurology, and general surgery. The $CO_2$ laser is also being used extensively for veterinarian surgery.

$CO_2$ lasers have several drawbacks. One drawback is the large and cumbersome dimensions of $CO_2$ lasers due to the size of $CO_2$ laser tubes. Another drawback is the long wavelength of the radiation produced by $CO_2$-type laser generators that makes it difficult to use fiber delivery devices/instruments (e.g., optical fibers) to couple and/or guide radiation produced by C02 laser generators to a target location, thus constraining the use of C02 laser generators with, for example, flexible endoscopes and bronchoscopes (which are configured to receive fiber delivery devices) to perform surgical applications in the interior of patients' bodies. Another drawback of the $CO_2$ laser is its relatively large spot size resulting from the large diffraction limit associated with the long wavelength of the radiation produced by such laser systems.

SUMMARY

In some embodiments, a laser system is disclosed that approximately achieves the same absorption levels typically produced by a $CO_2$ laser, avoids the challenges and difficulties presented by use of $CO_2$ laser systems, and has dimensions that make it convenient for surgical use. In some embodiments, the disclosed non-C02 laser systems that achieve the same or approximately the same absorption levels typically produced by a C02 laser can be used with flexible scope-based instruments (e.g., endoscopes, bronchoscopes) for inside-the-body surgical applications. In some embodiments, the laser systems described herein that achieve water absorption levels generally produced by C02 lasers have a spot size smaller than that produced with $CO_2$ lasers.

Accordingly, in some embodiments described herein, an improved laser system that achieves the same or approximately the same water absorption levels typically produced by a $CO_2$ laser, effectively overcoming the aforementioned difficulties and longstanding problems inherent in the use of $CO_2$ lasers, is provided. These problems have been solved in a simple, convenient, and highly effective way by which to achieve approximately the same water absorption levels typically produced by a $CO_2$ laser without using a $CO_2$ laser.

In some embodiments, a surgical laser is disclosed for achieving the approximate water absorption levels of those of a $CO_2$ laser without using a $CO_2$ laser.

In some embodiments, the disclosed systems and methods may include a non-$CO_2$ surgical laser that operates at wavelengths in the range of from about 2.4 μm to about 2.75 μm.

In one aspect, a surgical laser system is disclosed. The system includes a laser generator to generate laser radiation to cause water absorption levels that approximate water absorption levels achieved with a C02 laser, and one or more fibers coupled to the laser generator to deliver the generated laser radiation.

Embodiments of the device may include one or more of the following features.

The laser generator may include at least one laser diode. The at least one laser diode may include an array of laser diodes. The at least one laser diode may include at least one quantum-well laser manufactured using an Amimonide (Sb) compound. The at least one quantum-well laser may be manufactured using one of, for example, an In(Al)GaAsSb-based compound and/or a GaSb-based compound.

The laser generator may be configured to generate laser radiation having wavelengths in a range of between about 2.4 μm to about 2.75 μm.

The system may further include an optical transmitter coupled to the one or more fibers to direct the generated laser radiation to a target. The optical transmitter may include a collimating lens arrangement.

The one or more fibers may include one or more of, for example, a sapphire fiber and/or a germanate glass fiber.

The laser generator may include a specially doped fiber laser.

The laser generator may include a wavelength converter to convert a first generated laser radiation having a first wavelength to a resultant radiation having a resultant wavelength to be applied on a target. The wavelength converter may include an Optical-Parametric-Oscillation-based wavelength converter. The wavelength converter may be configured to convert the first generated laser radiation having the first wavelength to a resultant radiation having wavelengths in a range of between about 2.4 μm to about 2.75 μm.

The system may further include a scope to receive the one or more fibers, the scope being configured to be advanced through a body of a patient to a target area.

The laser generator may be configured to generate radiation at multiple possible wavelengths in a range of between about 2.4 μm to about 2.75 μm. The system may further include a controller to cause the generated laser radiation to have a particular wavelength selected from the multiple possible wavelengths in the range of between about 2.4 μm to about 2.75 μm. The laser generator may include multiple diode arrays, each of the diode arrays configured to emit radiation having a different one of the multiple possible wavelengths in the range. The controller may be configured to electrically actuate the multiple diode arrays based, at least in part, on user-provided input, to cause one of the multiple diode arrays to emit radiation having the selected particular wavelength.

In another aspect, a surgical laser system is disclosed. The system includes a laser device for producing a pumped laser beam, and an optical parametric oscillator (OPO) to convert the pumped laser beam into at least one resultant radiation component that, when applied to a target surface, causes water absorption levels that approximate water absorption levels achieved with a $CO_2$ laser.

Embodiments of the system may include one or more of the features described above in relation to the first system, as well as any of the following features.

The at least one resultant radiation component may include a signal component having a first wavelength and an idler component having a second wavelength.

The OPO may include a rotating crystal, wherein rotation of the crystal produces radiation components having differing wavelengths. The system may further include mirrors defining a cavity in which the OPO is disposed, the mirrors inhibiting passage of the signal radiation component wavelength and enabling passage of the idler radiation component.

One of the at least one resultant radiation component may have a wavelength in a range of between about 2.4 µm to about 2.75 µm.

The OPO may be configured to convert the pumped laser beam into at least one resultant radiation component at multiple possible wavelengths in a range of between about 2.4 µm to about 2.75 µm. The system may further include a controller to cause the at least one resultant radiation component to have a particular wavelength selected from the multiple possible wavelength in the range of between about 2.4 µm to about 2.75 µm. The controller may be configured to cause the at least one resultant radiation component to have a resultant wavelength selected from the range by controlling one or more of, for example, spatial position of the OPO and/or orientation of the OPO.

The system may further include one or more fibers to deliver the at least one resultant radiation component.

In a further aspect, a method is disclosed. The method includes generating laser radiation to cause water absorption levels that approximate water absorption levels achieved with a $CO_2$ laser, and delivering the generated laser radiation through one or more fibers.

Embodiments of the method may include one or more of the features described above in relation to the systems, as well as any of the following features.

Generating the laser radiation may include generating the laser radiation using at least one laser diode.

Generating the laser radiation may include generating laser radiation having wavelengths in a range of between about 2.4 µm to about 2.75 µm.

The method may further include transmitting to a target the laser radiation delivered through the one or more fibers. Transmitting to the target the laser radiation may include transmitting to the target the laser radiation delivered by the one or more fibers using a collimating lens arrangement coupled to the one or more fibers.

Generating the laser radiation may include converting a first generated laser radiation with a first wavelength to a resultant radiation having a resultant wavelength. Converting the first generated laser radiation may include converting the first generated laser radiation using an Optical-Parametric-Oscillation-based wavelength converter. Converting the first generated laser radiation may include converting the first generated laser radiation to a resultant radiation having a wavelengths in a range of between about 2.4 µm to about 2.75 µm.

The method may further include causing the generated laser radiation to have a particular wavelength selected from multiple possible wavelengths in a range of between about 2.4 µm to about 2.75 µm.

The systems, devices and methods described herein will be better understood by reference to the following detailed discussion of specific embodiments and the attached figures which illustrate and exemplify such embodiments.

BRIEF DESCRIPTION OF THE DRAWINGS

Embodiments of the present disclosure are described with reference to the following drawings.

DETAILED DESCRIPTION

The following disclosure described with reference to the drawings is illustrative of the systems, devices and methods and is not intended to limit the embodiments of the systems and methods encompassed by the claims of this application.

Disclosed herein are systems, devices and methods to generate laser radiation that can cause water absorption levels (when applied to a target) that approximate water absorption levels achieved with a $CO_2$ laser. The disclosed systems, devices and methods are implemented and/or practiced without using a $CO_2$ laser. In some embodiments, a surgical laser system that includes a laser generator (e.g., a laser generator implemented using at least one quantum-well laser diode, a laser generator implemented using a pump-laser device, etc.) to generate laser radiation to cause water absorption levels that approximate water absorption levels achieved with a $CO_2$ laser is disclosed. Coupled to the laser generator are one or more fibers to deliver the generated laser radiation. In some embodiments, the one or more fibers are coupled at their distal end to an optical transmitter, such as collimating lens arrangement. In some embodiments, the laser generator is configured to generate radiation at multiple possible wavelengths in a range of between about 2.4 µm to about 2.75 µm. Under such circumstances, the system further includes a controller (a tuner) to cause the generated laser radiation to have a particular wavelength selected from the multiple possible wavelengths in the range of between about 2.4 µm to about 2.75 µm.

Figure 1:
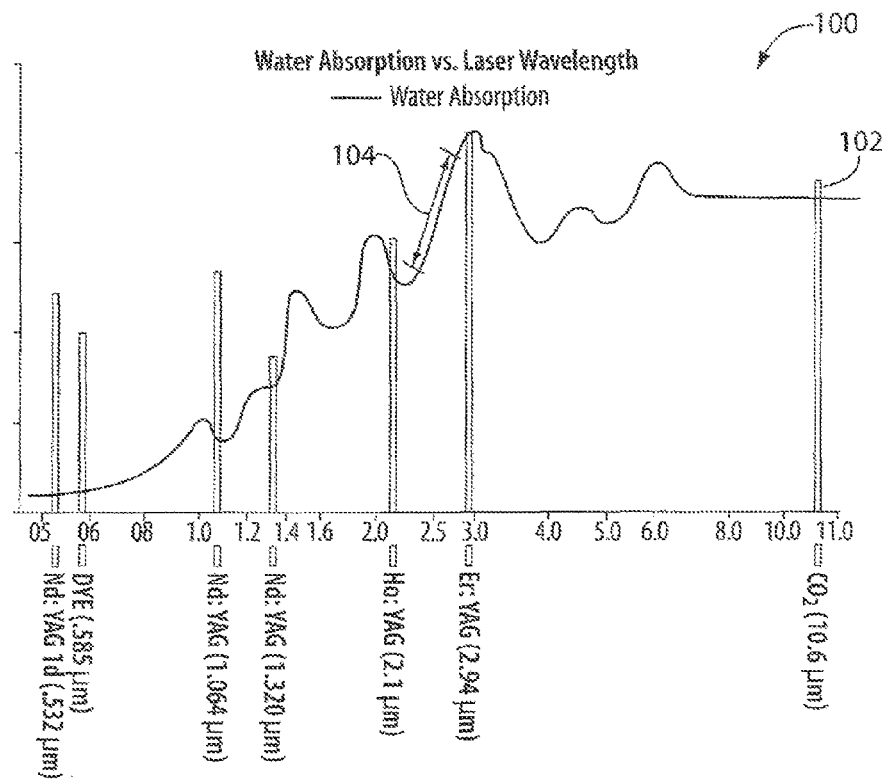
FIG. 1 is a graph illustrating water absorption vs. laser wavelength.

With reference to FIG. 1, a Water Absorption vs. Laser Wavelength graph 100 is shown depicting the relationship between laser wavelengths and water absorption levels. As illustrated in the graph of FIG. 1. $CO_2$ lasers operate at a wavelength of approximately 10.6 µm. The point on the graph marking the level of water absorption achieved by radiation having a wavelength of 10.6 µm is marked with reference numeral 102. Generally, the success of any laser used in tissue applications is the result of laser-tissue interaction at that wavelength that causes efficient water absorption levels. Different materials preferentially absorb the energy of different wavelengths. It is the preferential absorption of the energy of the wavelength of a $CO_2$ laser by body tissues that has been the hallmark of the success of $CO_2$ lasers.

The C02 laser removes tissue by a process called ablation. Ablation is the result of heat absorption and vaporization of the water in the tissue. Due to the fact that biological tissue is primarily water, the absorption of $CO_2$ laser energy is typically the result of water absorption. Generally, the absorbed heat may result in a thermally damaged zone adjacent to the ablated zone. The absorption coefficient (describing the extent to which the intensity of a radiation is reduced as it passes through a specific material) of radiation with the wavelength of the C02 laser is approximately 800 cm-$^1$. Such absorption characteristics typically lead to a depth of ablation of about 10 μm to about 20 μm. Such an ablation depth may be achieved in a single pass or in a few short pulses. As may be determined, for example, by a surgeon, multiple passes or multiple pulses of laser radiation application may be used. A comparable thermal damage zone will typically also occur. The depth of the thermal damage zone coagulates the blood in close proximity to the ablated zone. This allows for a finely controlled ablation zone with minimally thermal damage to adjacent tissue and with minimal blood perfusion during the operation.

The advantages of the C02 laser may be illustrated by contrasting the characteristics of a C02 laser to other commonly used lasers which operate at different wavelengths. For example, the Er:YAG laser that typically operates at 2.94 μm and has an ablation depth of 1 μm and a thermal damage zone of about 1-2 μm. Having a laser operating at this wavelength allows for extremely fine control of tissue ablation with minimum thermal damage. However, this laser, and the resultant generated radiation, has a drawback of performing tissue ablation operations at a relatively slow and somewhat inefficient manner. Another drawback of Er:YAG laser systems is that they do not efficiently coagulate the blood in the ablated tissue. On the other hand, a Ho:YAG laser that is used, for example, for urological applications, typically operates at 2.1 μm, has an ablation depth of about 380-400 μm and a thermal damage zone up to about 0.5 mm. This laser can thus ablate tissue relatively rapidly. However, this laser system suffers from the drawback that the thermal damage zone may be relatively large for applications in which precision is required.

Laser systems that generate radiation having a wavelength shorter than that provided by $CO_2$ laser systems (thus enabling delivery of the radiation using waveguide such as, for example, optical fibers), but which nevertheless would achieve water absorption level that approximate the level achieved with radiation generated by $CO_2$-based laser system would therefore enable performance of a greater range of surgical operations (e.g., operations employing scope-based instruments and the likes for interior body procedures). Thus, replacing the $CO_2$ laser and overcoming its drawbacks requires a system that: (1) would generate radiation causing an absorption depth of about 800 cm-$^1$; (2) would produce a wavelength that would be transmissible by glass or crystalline waveguides; (3) would generate sufficiently high power; and (4) would be compact and convenient for users (e.g., surgeons) to use.

Referring again to FIG. 1, water absorption levels comparable to those achieved at radiation having a wavelength of 10.6 μm (corresponding to radiation produced by a COrbased laser) may be achieved at radiation having wavelengths in the range of between about 2.4 μm to 2.75 μm. As can be seen from the graph 100, the segment 104, associated with a radiation wavelength range of between about 2.4 μm to about 2.75 μm, corresponds to water absorption levels that approximate the water absorption characteristics of radiation having a wavelength of 10.6 μm. Radiation with wavelengths in the range of between about 2.4 μm to about 2.75 μm thus fulfill at least enumerated characteristics 1 and 2 above, namely, an absorption coefficient approximately equal to 800 cm-$^1$, and wavelengths that are sufficiently short so that the radiation can be coupled to and transmitted by glass or crystalline waveguides.

The absorption depth at this range of wavelengths results in an absorption depth comparable to the absorption depth at 10.6 μm. Moreover, because the absorption spectra have a large slope at this wavelength range (i.e., the slope of the segment 104 is relatively pronounced), there is the additional benefit for operating at that wavelength range in that the absorption depth can be both tuned and controlled. Tuning and controlling the depth of absorption of the laser may result in additional control for laser-tissue interaction.

By using laser sources that can operate at the required wavelength range and have the potential of being high powered and compact, C02 laser systems may be replaced while still retaining the energy absorption characteristics of $CO_2$ lasers. Laser systems generating radiation with wavelengths in the range of about 2.4 μm to about 2.75 μm are not limited by the intrinsic lasing properties of the laser material and their lasing properties can be adjusted to required wavelengths.

Laser energy that replaces the $CO_2$ laser energy can be coupled and delivered to the remote locations using, for example, glass or crystalline fibers, Sapphire fibers, Germanate glass fibers, a combination of Germanate glass fibers with Sapphire tip and/or any other suitable waveguide or radiation conduits to deliver laser energy. In some embodiments, the waveguide is composed of Germanate glass fiber and fused silica tips. In some embodiments, the laser energy that replaces the $CO_2$ laser energy may be delivered in hollow core fibers. In some embodiments, the laser energy that replaces the $CO_2$ laser energy may be delivered without the use of fiber optics using arrangements comprising lens and/or mirror array, for example, such as those arrangements included in articulated arms conventionally used with C02 lasers.

Figure 2:
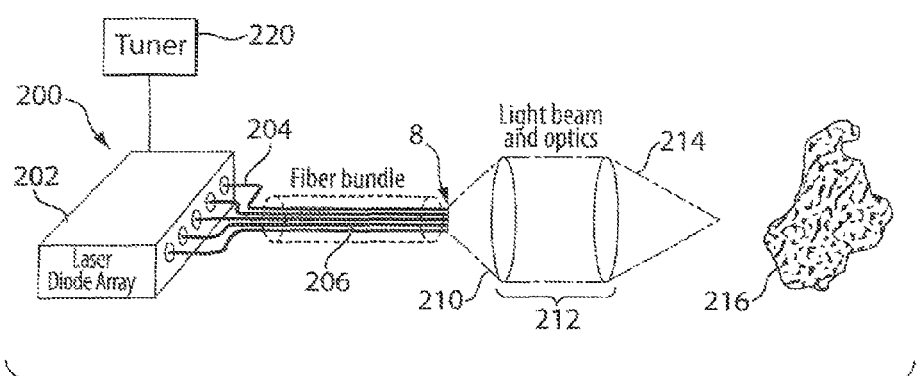
FIG. 2 is a schematic diagram of an exemplary laser system.

Referring to FIG. 2, a schematic diagram of an exemplary laser system 200 is shown. The laser system includes a laser generator 202 that is coupled to one or more fiber-type waveguides (e.g., optical or laser fibers). The laser generator is generally a non-C02 laser device. The laser generator 202 generates radiation having wavelength that can be coupled into fiber-type waveguides 204 configured to deliver the generated laser radiation from an entry point of the fibers (e.g., the ends of the one or more fibers proximate to the output port of the laser generator 202) to an exit point (e.g., the distal end of the one or more fibers through which radiation may be emitted). As noted, in some embodiments, the generated radiation coupled to the one or more fibers 204 has a wavelength in the wavelength range of between about 2.4 μm to about 2.75 μm such that wavelengths delivered by the one or more fibers 204, when applied to a target area (e.g., internal human tissue to be operated upon), can cause water absorption levels that approximate water absorption levels achieved with conventional $CO_2$ laser systems. The applied radiation having the wavelength in the above-specified range can therefore be used to perform ablation procedures, for example, resulting in ablated tissue that would similarly be produced had a conventional $CO_2$ laser system been used. The laser generator can be operated in either continuous wave mode or in a pulsed mode.

As further shown in FIG. 2, the one or more fibers 204 can be bundled to form a fiber bundle 206. The resultant fiber bundle 206 can be covered or encased in a protective shield or cover. As will be discussed in greater detail below, in some embodiment, the one or more fibers 204 can be placed in an scope, e.g., endoscope, or some other similar instrument having an inner channel, so that the one or more fibers 204 can be directed, via displacement of such a scope in the interior of, for example, a human body (or any other object) to an internal target area that otherwise would have been difficult to reach if the one or more fibers 204 were to be themselves directed to that target area. In contrast, due to the relative large size of $CO_2$ laser systems and/or the relatively long wavelength characteristics of radiation produced by such a system, it is generally difficult to direct that laser system, or a waveguide transmitting radiation produced by such $CO_2$ laser systems, to such hard-to-reach internal locations of the object upon which laser procedures are to be performed.

In some embodiments, the laser generator may include at least one laser diode, and may form a laser diode array. The at least one laser diode may include a quantum-well laser made on Antimonide (Sb) compounds such as, for example, In(Al) GaAsSb-based compounds, GaSb-based compounds, etc. Suitable laser devices based on laser diodes include laser diode manufactured, for example, by Power Photonic Corporation of Stony Brook, N.Y. In some embodiments, the laser generator may include a specially doped fiber laser such as, for example, erbium-doped fluorozirconate fibre laser. Other types of lasers, including pump lasers (described in greater details below), etc., may also be used.

The output radiation emitted from the distal end 208 of the one or more fibers 204 is typically a homogeneous radiation beam 210. In some embodiments, the homogeneous beam is directed to a collimator arrangement 212 to optically control the output radiation beam 210 (e.g., to narrow the path or projection of the beam 210). The collimator arrangement 212 may include a collimating lens arrangement, e.g., two sequential converging lenses. The resultant collimated beam 214 may then be focused upon a target area 216. For example, the target area 216 may be human tissue on which the beam may be applied to perform ablation operations. As noted, in some embodiments, lens arrangements, used in addition to or in place of fibers, to deliver radiation produced by the laser generator (in this case, the laser generator 202) may include arrangements included in articulated arms conventionally used with $CO_2$ lasers.

As noted, the laser generator, e.g., a laser generator comprising quantum-well laser diodes, can be manufactured to emit radiation in any wavelengths in the region of 2.4 µm to 2.75 µm. The particular wavelength(s) to be used may be selected according to the particular surgical application desired. For example, the wavelength may be selected according to the specific absorption level desired. The laser system 200 depicted in FIG. 2 may thus serve as a homogenizer for the output beam having a substantially homogeneous profile. In some embodiments, the laser system 200 may include a tuner or controller 220 configured to enable selection of a desired wavelength in a particular range (e.g., about 2.4 µm to about 2.75 µm) using a set of multiple diode arrays, each of which is configured (for example, on the basis of the specific material composition of the diode arrays) to emit radiation having a different wavelength within the above-specified range. In such implementations, the controller 220 may electrically actuate one of the diode arrays in the set to cause that diode array to be electrically excited and thus emit radiation having the particular wavelength for that array. In some embodiments, the controller may control a wavelength converter (e.g., a KTP crystal) to cause radiation emitted from the laser generator 202 (such radiation would typically have a specific wavelength) to be converted to the desired wavelength. The desired wavelength may be determined or specified through a user interface (not shown) that enables an operator (e.g., a surgeon) to specify the wavelength required.

Figure 3:
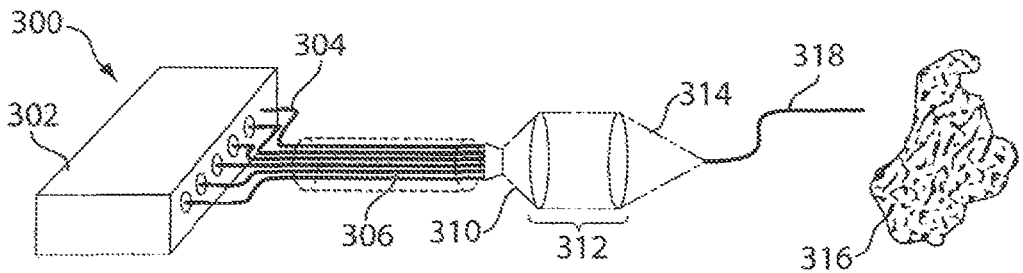
FIG. 3 is a schematic diagram of another exemplary laser system.

With reference to FIG. 3, a schematic diagram of another exemplary embodiment of a laser system 300 to generate radiation to cause water absorption level that approximate those that can be achieved with a $CO2$ laser system is shown. A laser generator 302, which may be similar to the laser generator 202 shown in FIG. 2, and which does not include a $CO_2$ laser device, is coupled to one or more fibers 304 that may be bundled together to form a fiber bundle 306. As with bundle 206 shown in FIG. 2, the bundle 306 may be covered or encased in a protective cover (or shield) to prevent physical damage to the fibers and/or to prevent degradation in performance due, for example, to ambient light or other external factors. In some embodiments, the laser generator 302 may include at least one laser diode made from, for example, a quantum-well laser made Antimonide (Sb) compounds such as In(Al)GaAsSb compounds, GaSb compounds, etc., manufactured, for example, by Power Photonic Corporation of Stony Brook, N.Y. Such laser diodes may be manufactured and/or structured to emit (when caused to operate) radiation having wavelengths in the range of about 2.4 µm to about 2.75 µm. The laser generator 302 may, in some embodiments, be coupled to and regulated by a controller (not shown in FIG. 3), which may be similar to the controller 220 shown in FIG. 2, to select the particular radiation wavelength to be used (e.g., a controller to select and control one of multiple diode arrays included with the laser generator 302). Emitted from the exit (output) ends of the one or more fibers 304 is a homogeneous, or coherent, beam 310. The homogeneous beam 310 is, in some embodiments, directed to a collimator arrangement 312, which may be similar to the collimator arrangement 212 depicted in FIG. 2.

As further shown in FIG. 3, in some embodiments, a resultant output collimated beam 314 may be focused upon an optical transmitter, for example, a fiber 318, to couple the optical radiation processed by the collimator arrangement 312 into the fiber 318. The fiber 318 is used to guide and direct the coupled optical radiation to a target 316 (e.g., human tissue on which radiation is to be applied). In some embodiments, the fiber 318 (or other types of optical transmitters) are inserted into a scope (e.g., into a working internal channel of an endoscope) and the scope maneuvered to the target location (e.g., an internal organ in the body that would otherwise be difficult to access with the fiber 318) to thus enable placement of output end of the fiber 318 proximate the target area. When the scope reaches the vicinity of the target area, the fiber 318 may be extended through an opening in the scope to bring the fiber close to the target area, and application of radiation on the target area may be commenced.

Figure 4:
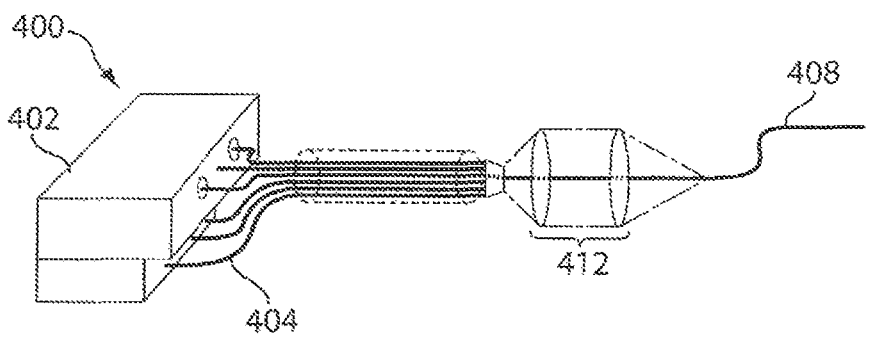
FIG. 4 is a schematic diagram of a further exemplary laser system.

Referring to FIG. 4, a schematic diagram of an exemplary embodiment of a laser system 400 to generate radiation to cause water absorption levels that approximate those that can be achieved with a $CO_2$ laser system is shown. The system 400 includes a laser generator 402 that includes, in some embodiments, a single emitter, and a fiber 404 into which radiation produced by the emitter is coupled. In some embodiments, the laser generator may include multiple output ports for a particular single type emitter (i.e., all the diodes emitters are configured to produce radiation having substantially the same wavelength) such that an output radiation coupled to the fiber 404 corresponds to the combined output of the radiation produced by each of multiple laser diodes. In some embodiments, the emitter may have a single output port. The emitter may be similar in structure and operation to any of the laser diodes in the laser diode arrays of laser systems 202 and 302 shown in FIGS. 2 and 3, respectively. Thus, the emitter may include a quantum-well laser based on Antimonide (Sb) compounds, such as, for example, In(Al)GaAsSb-based compounds, GaSb-based compounds, etc., and may be configured to emit radiation in the range of about 2.4 µm to about 2.75 µm. Use of a single laser diode instead of a diode array enables compactness and ease of fiber coupling (i.e., coupling of radiation generated by the emitter to the fiber). However, the use of a single diode instead of multiple diodes (e.g. arranged as an array) may result in a lower level of power than what may be needed to perform a laser-based procedure. The output of the emitter is coupled to one or more fibers (which may be similar to the one or more fibers 204 and/or 304 shown in FIGS. 2 and 3), and the radiation delivered by the one or more fibers 404 may in turn be coupled to a collimator arrangement 412 and/or an optical transmitter 408, before being applied onto the target area. The output of the fiber is used to direct the light onto a target (not shown).

Figure 5:
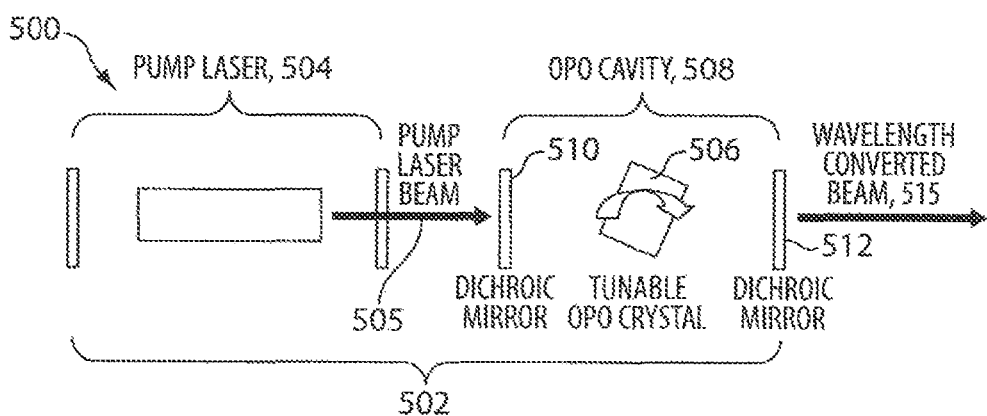
FIG. 5 is a schematic diagram of another exemplary laser system.

Referring to FIG. 5, a schematic diagram of an exemplary embodiment of a laser system 500 to generate radiation (e.g., laser radiation) to cause water absorption levels that approximate radiation absorption levels those that can be achieved using a $CO_2$ laser system is shown. In some embodiments, a laser generator includes a laser device generating a first laser radiation having a first wavelength and a wavelength converter to convert the first generated radiation to a resultant radiation having a resultant wavelength. The resultant radiation is subsequently applied to the target area to be treated. This wavelength conversion may be performed based on an optical phenomenon referred to as Optical Parametric Oscillation (OPO). OPO relies on a nonlinear response of a medium to a driving field, such as a pump laser beam, to convert an input radiation (photons) having one wavelength into one or more (e.g. two) radiation components having different (longer) wavelengths. In circumstances where two radiation components are produced through the interaction of the input radiation with the converting medium, one component is referred to as the Signal component and one component is referred to as the Idler component. Typically, a high energy photon (short wavelength) may be split into two low energy photons (having longer wavelengths). The conversion medium may be a nonlinear crystal (BBO or KTP or Periodically Poled KTP) put into the laser beam path. Suitable nonlinear crystals include those made by Raicol Ltd., Israel. Use of nonlinear crystals to convert optical wavelengths enables wavelength conversion from, for example, a conventional 1.06 µm Nd:YAG laser to radiation having wavelengths of up to 4 µm with power conservation efficiencies of 15% to 50% depending on the wavelength and laser device. The relationship between the input radiation and the output radiation components can generally be represented as:

$$1/\text{A.input} = 1/\text{A.signal} + 1/\text{A.Idler}$$

where A.input is the wavelength of the input radiation, A.signal is the wavelength of the resultant Signal component and A.Idler is the wavelength of the Idler component.

The wavelengths of the Signal and idler wavelengths are determined, at least in part, based on the angle the input radiation generated by the laser device (e.g., the pump laser) makes with the tunable OPO crystal's axis. Accordingly, rotation of the medium (crystal) to place it in different orientations will result in different wavelengths for the resultant radiation.

Furthermore, when the tunable medium is placed in a resonant cavity (as depicted in the arrangement of FIG. 5), feedback (achieved, for example, using two dichroic mirrors) may cause a gain to be achieved in the parametric waves in a process that is similar to a build up in a laser cavity. Light output at the resonated wavelength (and the simultaneously produced other parametric wavelengths) may then occur.

Thus, as shown in FIG. 5, in some embodiments, the laser system includes a laser generator 502 that may include a laser device 504, that is generally a non-$CO_2$ laser device, to generate the initial radiation. The laser generator also includes a wavelength converter 506, e.g., an OPO crystal, to convert the wavelength of the input radiation into two or more output components. A suitable laser device to generate the initial radiation having the first wavelength may be a pump laser device such as a Nd:YAG laser that is configured to generate radiation having, for example, a wavelength of 1064 nm (1.064 µm), but may also generate radiation of, for example, 946, 1120, 1321, 1440 nm, etc. Such a laser device may be configured to operate to continuous mode or in pulsed-mode, e.g., a Q-switched Nd:YAG laser operating in the infrared spectrum having pulse widths of, for example, less than 5 nanoseconds. A laser operating in pulsed mode, e.g., a Q-switched Nd:YAG, may include an optical switch that is inserted in the laser cavity that opens upon reaching a maximum population inversion (i.e., achieving a state in which sufficient atoms in the laser cavity are in an excited state), to thus generate an emission of one or more pulses. Other suitable laser devices, including, for example Nd:YLF lasers, Yb:YAG lasers, etc., may also be used. In some embodiments, one or more laser diodes may be used to generate the initial radiation having the first wavelength.

With continued reference to FIG. 5, radiation 505 generated by, for example, the laser device 504 (e.g., a pump laser device) is directed through a dichroic mirror 510 into an OPO cavity 508 (defined by the mirror 510 and a second dichroic mirror 512) in which a rotatable wavelength converter 506 (for example, a non-linear crystal medium that causes an incident input radiation to be converted into one or more resultant radiation waves) is disposed. The tunable wavelength converter may be controlled by a controller (not shown in FIG. 5) that regulates the position and/or orientation of the wavelength converter. Such a controller may include an interface to enable a user to specify a desired wavelength (alternatively and/or additionally, pre-programmed specifications for desired wavelengths may be stored on a memory device comprising part of the controller). Such a controller may actuate a motor (e.g., a stepper motor) based on the wavelength required to be generated to cause the motor to rotate or otherwise displace the wavelength converter. Other types of displacement mechanisms to control the orientation/position of the wavelength converter (in implementations in which the converter is, for example, a non-linear converting medium) may be used.

Having controlled the wavelength converter to cause it to be spatially oriented and/or spatially positioned so that one or more resultant radiation components having desired wavelengths would be generated in response to an input radiation having particular wave characteristics (e.g., a wavelength of 1.064 µm, and a particular pulse width), the laser device 504 of the laser generator 502 may be activated to cause the resultant radiation components at the output of the wavelength converter 506 to be generated. As described herein, in some embodiments, at least one of the generated resultant radiation components, e.g., the Signal component, may have a wavelength of between about 2.4 µm to about 2.75 µm. In other words, the wavelength converter is controlled to spatially orient/position it so that it causes at least one radiation component having a wavelength in the above-specified range to be generated. As previously explained, radiation having a wavelength of between about 2.4 µm to about 2.75 µm will cause water absorption levels that approximate the water absorption levels that can be achieved using a $CO_2$ laser device.

The two dichroic mirrors 510 and 512 are generally configured such that photons of Signal radiation component are reflected and circulate within the OPO cavity 508, whereas the photons of the Idler component generally pass through, for example, the second dichroic mirror and can thus escape the cavity. The radiation beam of the Signal Component may thus be amplified via repeated reflections within the cavity 508 and interactions with the input radiation beam (produced, for example, by the pump laser device) inside the OPO wavelength converter 506.

The resultant Signal radiation component 515 having the desired wavelength (e.g., between about 2.4 µm to about 2.75 µm) is coupled out of the OPO cavity 508 and from there it can be delivered (via, for example, one or more fibers, not shown in FIG. 5, that may be similar, for example, to the one or more fibers 204, 304 and 404 shown in FIGS. 2, 3 and 4, respectively) to the target area to be treated.

As noted, any one of the laser systems described herein may further include a scope-based device to enable performance of various procedures (e.g. surgical procedures) within the interior of the target object. In some embodiments, a flexible endoscope (e.g., bronchoscope, urethroscope, etc.) may be used for the treatment procedures, e.g., a laparoscopic procedure. An endoscope is a tool which is usually passed through a natural orifice of the body (mouth, nose, rectum, vagina, urethra), or through an incision made on the body, to view the inside of the body. For example, an endoscope may be passed through an incision in the abdominal wall. Prior to or subsequent to the insertion of the flexible endoscope, a fiber-based tool, for example, the one or more fibers 204, 304 and/or 404 described herein in relation to FIGS. 2-4, respectively, may be passed through the interior channel (also referred to as the working channel) defined in the scope.

Figure 6:
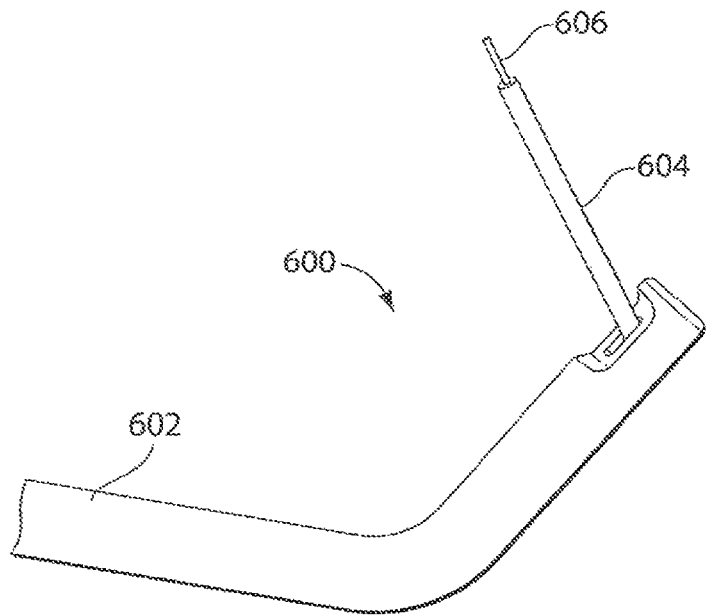
FIG. 6 is a schematic diagram of an exemplary laser system that includes a scope-based device.

With reference to FIG. 6, a diagram of a device 600 that includes a first scope 602, e.g., a flexible endoscope, containing a smaller second scope 604 (sometimes referred to as the baby scope) is shown. In some embodiments, the second smaller scope may include one or more laser fibers 606 such as the laser fibers 204, 304 and/or 404 shown, respectively, in FIGS. 2-4. The first scope 602 may be advanced through a body of a patient and be positioned so that an opening at its distal end is proximate the target area to be treated by the one or more fibers. The second (baby) scope may then be extended from within the first scope to a location near the target area, and once extended the one or more fibers 606 may be extended or slid out. Once the one or more fibers 606 has been extended out, a laser generator (not shown in FIG. 6), such as, for example, any one of the laser generators 202, 302, 402 and 502 depicted in FIGS. 2-5, respectively, may be activated to couple radiation having wavelengths in the range of, for example, between about 2.4 µm to about 2.75 µm. Radiation having a wavelength in this range is coupled into the one or more laser fibers 606 and irradiated from the distal end of the one or more fibers 606 on a target area to be treated. The irradiated radiation, having a wavelength of, for example, between about 2.4 µm to about 2.75 µm, can thus cause water absorption levels in the treated area that approximate the water absorption levels that can be achieved with a C02 laser system.

Figure 7:
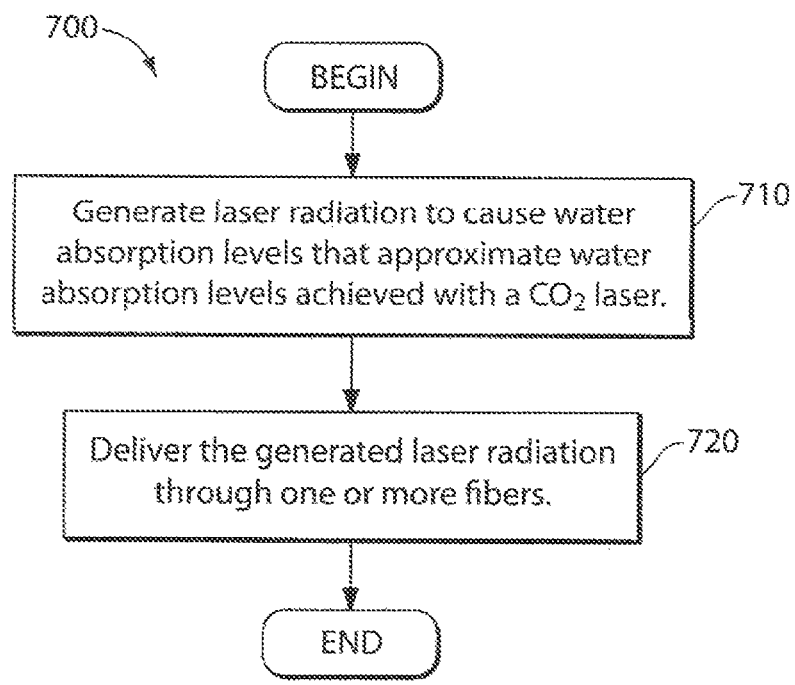
FIG. 7 is a flowchart of an exemplary procedure to perform laser operations.

Referring to FIG. 7, a flowchart of an exemplary procedure 700 to perform laser-based operations is shown. In some embodiments, laser radiation to cause water absorption levels that approximate water absorption levels achieved with a $CO_2$ laser is generated 710. The laser radiation is generally generated using a non-$CO_2$ laser device. For example, the radiation may be generated using at least one laser diode that may include a quantum-well laser based on Antimonide (Sb) compounds such as, for example, In(Al)GaAsSb-based compounds, GaSb-based compounds, etc. In some embodiments, the radiation has a wavelength of between about 2.4 µm to about 2.75 µm. In some embodiments, the generated laser radiation is controlled (e.g., using a controller) to have a particular wavelength selected from multiple possible wavelengths in a range of between about 2.4 µm to about 2.75 µm. In some embodiments, the radiation may be generated using a pump laser that produces radiation at a relatively short wavelength, and which subsequently is passed through a wavelength converter (e.g., a non-linear crystal) to produce one or more radiation components with converted wavelengths in the range of, for example, between about 2.4 µm to about 2.75 µm.

The generated radiation is then delivered 720 through waveguides, e.g., one or more fibers, to the target area to be treated. In some embodiments, the waveguides include glass or crystalline fibers, Sapphire fibers, Germanate glass fibers, a combination of Germanate glass fibers with Sapphire tip and/or any other suitable waveguide or radiation conduits to deliver laser energy.

In some embodiments, radiation delivered via the one or more waveguide may be coupled to another optical transmitter(s) such as, for example, a collimating lens arrangement. In some embodiments, the one or more fibers may be placed in one or more scope-based devices (e.g. an endoscope) to enable placement of the one or more fibers proximate to areas that are located in the interior of the object being operated upon (e.g., a patient's body).

A number of embodiments of the invention have been described. Nevertheless, it will be understood that various modifications may be made without departing from the spirit and scope of the invention. Accordingly, other embodiments are within the scope of the following claims.

What is claimed is:

1. A surgical laser system comprising:
    a laser generator configured to generate laser radiation;
    one or more fibers coupled to the laser generator to deliver the generated laser radiation;
    wherein the surgical laser system is configured to apply the generated laser radiation to a target at wavelengths between 2.4 µm and 2.75 µm to cause water absorption levels that approximate water absorption levels achieved with a $CO_2$ laser; and;
    wherein the laser generator comprises at least one laser diode, the laser diode comprising at least one quantum-well laser manufactured using an Antimonide (Sb) compound.

2. The system of claim 1 wherein the at least one quantum-well laser is manufactured using one of an In(Al)GaAsSb-based compound and a GaSb-based compound.

3. The system of claim 1 wherein the at least one laser diode comprises an array of laser diodes.

4. The system of claim 1 wherein the laser generator is configured to generate the laser radiation with wavelengths between 2.4 µm and 2.75 µm.

5. The system of claim 1 further comprising an optical transmitter coupled to the one or more fibers to direct the generated laser radiation to a target.

6. The system of claim 5 wherein said optical transmitter comprises a collimating lens arrangement.

7. The system of claim 1 wherein the one or more fibers comprise one or more of:

sapphire fiber and a germanate glass fiber.

8. The system of claim 1 wherein the laser generator comprises a specially doped fiber laser.

9. The system of claim 1 wherein the laser generator comprises:

a wavelength converter to convert a first generated laser radiation having a first wavelength to a resultant-laser radiation having a resultant wavelength to be applied to the target.

10. The system of claim 9 wherein the wavelength converter comprises an Optical-Parametric-Oscillation-based wavelength converter.

11. The system of claim 9 wherein the wavelength converter is configured to convert the first generated laser radiation having the first wavelength to a resultant radiation having wavelengths between 2.41 μm and 2.75 μm.

12. The system of claim 1 further comprising:

a scope to receive the one or more fibers, the scope configured to be advanced through a body of a patient to a target area.

13. The system of claim 1 wherein the laser generator is configured to generate radiation at multiple possible wavelengths between 2.4 μm and 2.75 μm, and wherein the system further comprises a controller to cause the generated laser radiation to have a particular wavelength selected from the multiple possible wavelengths between 2.4 μm and 2.75 μm.

14. The system of claim 13 wherein the laser generator includes multiple diode arrays, each of the diode arrays configured to emit radiation having a different one of the multiple possible wavelengths between 2.4 μm and 2.75 μm, and wherein the controller is configured to electrically actuate the multiple diode arrays based, at least in part, on user-provided input, to cause one of the multiple diode arrays to emit radiation having the selected particular wavelength.

15. A method of using the surgical laser system of claim 1, comprising:

generating laser radiation using the laser generator; and delivering the generated laser radiation through the one or more fibers to a target at wavelengths between 2.4 μm and 2.75 μm to cause water absorption levels that approximate water absorption levels achieved with a CO2 laser.

\* \* \* \* \*